US009090804B2

(12) United States Patent
Tegen et al.

(10) Patent No.: US 9,090,804 B2
(45) Date of Patent: Jul. 28, 2015

(54) METHODS FOR GENERATING MIXTURES OF DIISOCYANATES BY PHOSGENATION OF DIAMINO ALKYL ESTERS

(75) Inventors: Mark G. Tegen, Gig Harbor, WA (US); William Rusty Sutterlin, Hoover, AL (US)

(73) Assignee: Inventure Renewables, Inc., Tuscaloosa, AL (US)

( * ) Notice: Subject to any disclaimer, the term of this patent is extended or adjusted under 35 U.S.C. 154(b) by 180 days.

(21) Appl. No.: 13/819,299

(22) PCT Filed: Aug. 16, 2011

(86) PCT No.: PCT/US2011/047971
§ 371 (c)(1),
(2), (4) Date: Mar. 27, 2013

(87) PCT Pub. No.: WO2012/027162
PCT Pub. Date: Mar. 1, 2012

(65) Prior Publication Data
US 2013/0209729 A1    Aug. 15, 2013

Related U.S. Application Data

(60) Provisional application No. 61/377,727, filed on Aug. 27, 2010.

(51) Int. Cl.
| | |
|---|---|
| *C07C 267/00* | (2006.01) |
| *C09J 197/02* | (2006.01) |
| *C07C 263/10* | (2006.01) |
| *C07C 265/14* | (2006.01) |
| *C08G 18/72* | (2006.01) |
| *C08G 18/77* | (2006.01) |
| *C08L 97/02* | (2006.01) |

(52) U.S. Cl.
CPC ............ *C09J 197/02* (2013.01); *C07C 263/10* (2013.01); *C07C 265/14* (2013.01); *C08G 18/721* (2013.01); *C08G 18/771* (2013.01); *C08L 97/02* (2013.01); *Y10T 428/24066* (2015.01)

(58) Field of Classification Search
CPC .................................................... C07C 263/10
See application file for complete search history.

(56) References Cited

U.S. PATENT DOCUMENTS

| | | | | |
|---|---|---|---|---|
| 3,281,378 | A | * | 10/1966 | Gasser et al. ................. 521/124 |
| 3,465,023 | A | * | 9/1969 | Kamal .......................... 560/347 |
| 4,539,157 | A | | 9/1985 | Dewhurst et al. |
| 5,407,980 | A | | 4/1995 | Pizzi et al. |
| 6,900,348 | B1 | * | 5/2005 | Reif et al. .................... 560/347 |
| 2005/0222453 | A1 | * | 10/2005 | Woelfert et al. ............. 560/347 |
| 2006/0231968 | A1 | | 10/2006 | Cowan et al. |
| 2007/0012577 | A1 | * | 1/2007 | Bulan et al. .................. 205/431 |
| 2009/0012202 | A1 | | 1/2009 | Jacobine |

OTHER PUBLICATIONS

Hong, Sung Ran, Search Report issued in PCT/US2011/047971, Apr. 9, 2012.
Hong, Sung Ran, Written Opinion issued in PCT/US2011/047971, Apr. 9, 2012.

* cited by examiner

*Primary Examiner* — Michael L Leonard
(74) *Attorney, Agent, or Firm* — Gregory P. Einhorn; Greer Burns & Crain, Ltd.

(57) ABSTRACT

The present invention relates to an improved composition comprising a blend of diisocyanates of Formula (II) derived from their corresponding dianiino alkyl esters obtained from soy protein source, wherein R is an alkyl and n is 1-4, and methods of making and using such compositions as construction material resin binders, in particular, wood resin binders and/or adhesives.

(II)

R = alkyl
n = 1-4

20 Claims, No Drawings

METHODS FOR GENERATING MIXTURES OF DIISOCYANATES BY PHOSGENATION OF DIAMINO ALKYL ESTERS

CROSS-REFERENCE TO RELATED APPLICATIONS

This United States utility patent application is the §371 national phase of PCT international patent application no. PCT/US2011/047971, having an international filing date of Aug. 16, 2011, which claims the benefit of priority to U.S. Provisional Patent Application Ser. No. 61/377,727 filed on Aug. 27, 2010, which aforementioned applications are expressly incorporated herein by reference in their entirety and for all purposes.

INCORPORATION BY REFERENCE

Any foregoing applications and all documents cited therein or during their prosecution ("application cited documents") and all documents cited or referenced m the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by referenced herein, are hereby incorporated herein by reference, and may be employed, in the practice of the invention.

Citation or identification of any document in this application is not an admission that such document is available as prior art to the present invention.

FIELD OF THE INVENTION

The invention relates to compositions comprising diisocyanates derived from their corresponding diamino alkyl esters and methods of making and using the same. In one embodiment the invention relates to the compositions comprising mixtures of diisocyanates prepared from soy protein for use as wood binders.

BACKGROUND Of THE INVENTION

For many years, fiberboards have been manufactured from wood or agricultural substrates using thermosetting binders. Formaldehyde-based binders, such as urea formaldehyde and melamine formaldehyde have traditionally dominated the fiberboard industry during that time. Wood composites made with an adhesive binder containing a formaldehyde-based resin have generally been limited to applications where exterior durability is not required. Unfortunately, one of the drawbacks of using formaldehyde-based resins as a component of wood composite adhesive binders is that such resins may release a small amount of formaldehyde.

Isocynate-based binders, particularly diphenylmethane diisocyanate (MDI) binders, however, offer some significant advantages over formaldehyde-based binders, including superior physical and moisture-resistance properties and the elimination of formaldehyde emission hazards. Although isocyanate binder technology for fiberboard manufacture has been available for many years, isocyanates have not gained widespread commercial acceptance, primarily because of cost. MDI-based isocyanates tend to be more expensive per pound than formaldehyde-based binders, but are used at a lower dose rate, partially offsetting the cost disadvantage.

As such, there is a continuing need for identifying new adhesive binder compositions suitable for making wood and other composites, which have an improved physical properties and are safe to use.

SUMMARY OF THE INVENTION

The present invention relates to an improved composition comprising a blend of diisocyanates of Formula (II) derived from their corresponding diamino alkyl esters of Formula (I), obtained from soy protein source, wherein R is an alkyl and n is 1-4, and methods of making and using such compositions as construction material resin binders.

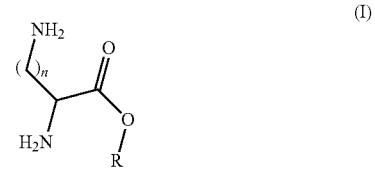

R = alkyl
n = 1-4

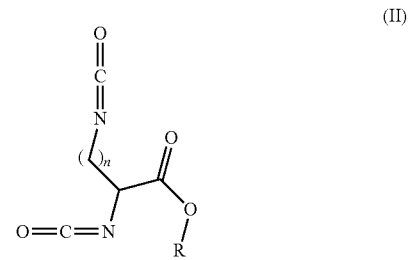

R = alkyl
n = 1-4

In one embodiment the Invention relates to a composition, comprising a mixture of diisocyanates.

Another embodiment of the present invention is directed to a method of making diisocyanates by treating the soy-based diamino alkyl esters with phosgene.

In another embodiment, the present invention relates to the use of a composition comprising diisocyanates prepared from soy-based material as wood resin binders.

Provided are methods of preparing a mixture of at least two diisocyanates comprising: (a) providing protein source comprising or derived from soy protein, corn, rice bran, or oil seeds; (b) processing the protein source to generate a product comprising a biodiesel biofuel and a water/glycerin fraction comprising a mixture of alkyl esters comprising diamino alkyl esters and monofunctionalized alkyl esters; (c) separating from the water/glycerin fraction the monofunctionalized alkyl esters to generate a product comprising diamino alkyl esters, and (d) reacting the separated mixture of diamino alkyl esters of step (c) with an excess of a phosgene to generate a mixture of diisocyanate derivatives of Formula II

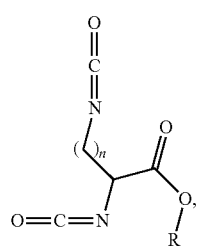

(II)

wherein R is an alkyl, and n=1–4
wherein the reaction to generate a mixture of diisocyanate derivatives from the mixture of diamino alkyl esters comprises conditions of temperatures between about 50 to 200° F. and pressures of between 1 to 10 bar.

Provided are methods of preparing a mixture of at least two diisocyanates wherein at least one of the diisocyanates produced is an alkyl 2,6-diisocyanatohexanoate, an alkyl 2,3-diisocyanatopropanoate, an alkyl 5-(3 formylguanidino)-2-isocyanatopentanoate, or an alkyl 2,4-diisocyanatobutanoate.

Provided are methods of preparing a mixture of at least two diisocyanates wherein at least one of the diisocyanates produced is a methyl 2,6-diisocyanatohexanoate, a methyl 2,3-diisocyanatopropanoate, a methyl 5-(3-formylguanidino)-2-isocyanalopentanoate, or a methyl 2,4-diisocyanatobutanoate.

Provided are methods of preparing a mixture of at least two diisocyanates wherein the naturally occurring protein source comprises a soy protein source, a corn, a rice bran, an oil seed, an algae, a grain, a sorghum, or a combination thereof.

Provided are methods of preparing a mixture of at least two diisocyanates wherein the mixture of diamino alkyl esters is reacted with an excess of a di-phosgene, a tri-phosgene or both, to generate a mixture of diisocyanate derivatives from the mixture of diamino alkyl esters.

Provided are methods of preparing a mixture of at least two diisocyanates wherein the mixture of diamino alkyl esters comprises a diamino methyl ester.

Provided are methods of preparing a mixture of at least two diisocyanates wherein the mixture of diamino alkyl esters comprises the diamino alkyl esters of a lysine, an asparagine, an arginine and a glutamine.

Provided are methods of preparing a mixture of at least two diisocyanates wherein the separating of the 50% monofunctionalized alkyl esters from the water/glycerin fraction comprises use of an ion exchange or a chromatographic separation.

Provided are methods of preparing a mixture of at least two diisocyanates wherein the separating of the 50% monofunctionalized alkyl esters from the water/glycerin fraction comprises use of a batch or a continuous mode process.

Provided are methods of preparing a mixture of at least two diisocyanates wherein a product comprising the mixture of diamino alkyl esters is generated by reacting a feedstock source with an alcohol under pressure.

Provided are methods of preparing a mixture of at least two diisocyanates wherein the process comprises reacting the feedstock source with an alcohol and an acid in a pressure reactor system that allows for sufficient temperature to keep the alcohol from boiling in the presence of an acid catalyst.

Provided are methods of preparing a mixture of at least two diisocyanates wherein the pressure in the pressure reactor system is 20 PSIG over the vapor pressure of the alcohol.

Provided are methods of preparing a mixture of at least two diisocyanates, further comprising mixing or formulating the mixture of diisocyanate derivatives with a silica, a wax, an antifoamer, a lubricant, a plasticizer, a softening agent, a pigment, a biocide, a filler or a combination thereof.

Provided are methods of preparing a mixture of at least two diisocyanates, further comprising making a manufactured material or a product of manufacture using or incorporating the mixture of diisocyanate derivatives.

Provided are methods of preparing a mixture of at least two diisocyanates wherein the manufactured material or the product of manufacture is: an oriented strand board (OSB), a medium density fiberboard (MDF), a plywood panel or a wood-based composite panel, a flexible foam seating material, a rigid foam insulation panel, a microcellular foam seal, a microcellular foam gasket, a durable elastomeric wheel, a durable elastomeric tire or an automotive suspension bushing, an electrical potting compound, an adhesive, a sealant, a fiber, seal, a gasket, a carpet underlay, or a hard plastic part.

It is further noted, that the invention does not intend to encompass within the scope of the invention any previously disclosed product, process of making the product or method of using the product, which meets the written, description and enablement requirements of the USPTO (35 U.S.C. 112, first paragraph) or the EPO (Article 83 of the EPC), such that applicant(s) reserve the right and hereby disclose a disclaimer of my previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention.

These and other embodiments axe disclosed or are apparent from and encompassed by, the following Detailed Description.

DETAILED DESCRIPTION OF THE INVENTION

The present invention relates to a novel diisocyanate-based-based composition, and particularly an amino acid derived diisocyanate-based composition, wherein the amino acid derived diisocyanates of Formula (II) are prepared by phosgenation of diamino alkyl esters of Formula (I) obtained from soy protein as shown in Reaction Scheme I below. Such compositions can be used for binding various materials, such as, for example, wood, foam, plastic, etc., used in construction, automotive, and, other industries.

Reaction Scheme I

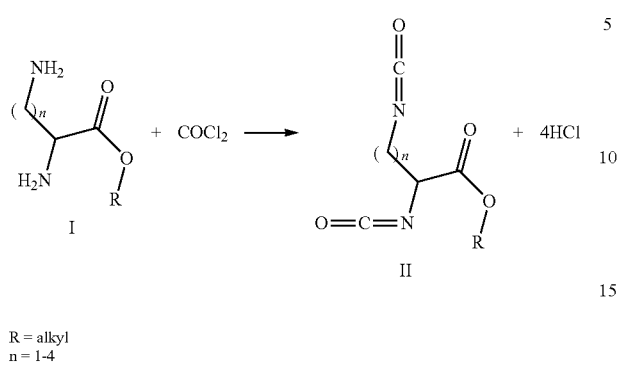

R = alkyl
n = 1-4

Alkyl as referred herein is a straight or branched chain saturated hydrocarbon having one to six carbons, preferably one to three carbons, and which cast be further substituted.

The carbon chain between the two amino groups in Formulas (I), having one to four carbons (n=1-4), can be further substituted at any position of the chain.

One of the embodiments of the present invention is directed to a composition comprising at least two, at least three, or at least four diisocyanates.

Another embodiment of the present invention is directed, to a composition comprising at least two diisocyanates selected from the group consisting of alkyl 2,3-diisocyanatopropanoate (Formula II-1), alkyl 2,4-diisocyanatobutanoate (Formula II-2), alkyl 5-(3-formylguanidino)-2-isocyanatopentanoate (Formula II-3), and alkyl 2,6-diisocyanatohexanoate (Formula II-4) as shown below:

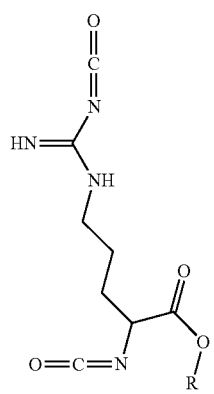

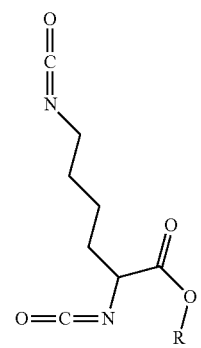

R = alkyl

Another embodiment of the present invention is directed to a composition comprising at least two diisocyanates selected from the group consisting of methyl 2,3-diisocyanatopropanoate (II-5) methyl 2,4-diisocyanatobutanoate (II-6), methyl 5-(3-formylguanidino)-2-isocyanatopetanoate (II-7), and methyl-2,6-diisocyanatohexanoate (II-8) as shown below.

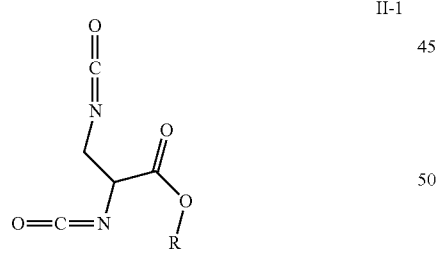

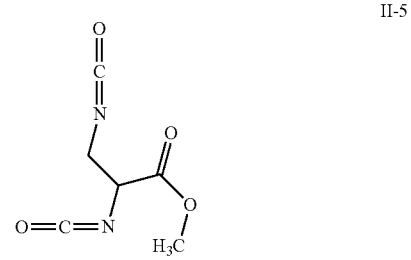

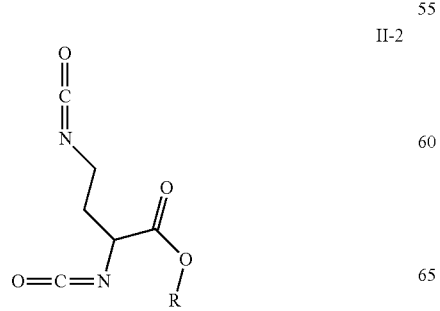

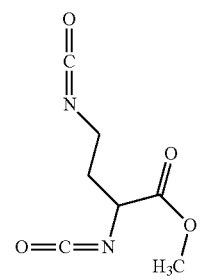

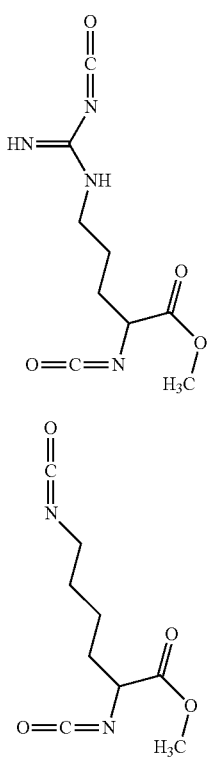

The diisocyanates of the present invention include, but are not limited to the derivatives of lysine, asparagine, arginine, and glutamine.

The composition of the present invention, if used as an adhesive binder composition, may also contain a variety of other known additives such as, for example, silica to enhance fire resistance, wax to enhance water resistance, antifoamers, lubricants, plasticizers, softening agents, pigments, biocides, fillers, and the like.

According to the present invention, a mixture of diisocyanates can be prepared by reacting diamino alkyl esters of the corresponding amino acid derivatives with di- or triphosgene as shown in Reaction Scheme I. The alkyl esters can be obtained from soy protein or other naturally occurring protein source, such as corn, rice bran, oil seeds and the like. The diamino alkyl esters can be also obtained from other inexpensive sources of proteins, such as, for example algae, various grains and oil seeds, corn, sorghum, and the like.

The mixtures of amino methyl esters suitable for such modification can be obtained, for example, from the process of making biodiesel, as described in U.S. patent application Ser. No. 12/243,933, which is incorporated herein by reference in its entirety. The water/glycerin fraction produced with the biofuel also contains diamino alkyl esters. About 50% of these alkyl esters are separated as they would only make monofunctional isocyanates, which can be further utilized after being converted to the corresponding amino acids or amino alcohols. The separation of mono- and difunctionalized alkyl esters (or methyl esters) for use in the present invention can be achieved through ion exchange, or chromatographic separation. This process can be done in a batch or a continuous mode typically at ambient temperature and pressure. The target diamino alkyl esters comprising lysine, asparagine, arginine, and glutamine residues are about 50% of the soy protein by mass.

Upon separation from monofunctionalized isocyanates, various mixtures of diamino alkyl esters of Formula (I) are treated with an excess of phosgene (di or tri) to give diisocyanate derivatives of Formula (II) and 4 moles of HCl as exemplified in Reaction Scheme I. This process can be carried out at temperatures of about 50 to about 200° F. and at pressures ranging from about 1 to about 10 bar.

Without being bound by any theory, the diisocyanates of the improved diisocyanate-based adhesive composition of the present invention can polymerize with molecules in wood fibers and other materials containing "active" hydrogens to produce corresponding polyurethane based molecules, which provide an improved toughness, durability and safety profile to wood composites or other materials.

One of the embodiments of the present invention relates to compositions comprising a mixture of at least two diisocyanates for use as resin binders in wood products, which include but are not limited to particle boards, such as for example, oriented strand boards (OSB) and medium density fiberboards (MDF).

Diisocyanate resin binders of the present invention can be also used in the manufacturing of other materials and products, which include, but are not limited to flexible foam seating materials, rigid foam insulation panels, microcellular foam seals, microcellular foam gaskets, durable elastomeric wheels, durable elastometric tires, automotive suspension bushings, electrical potting compounds, adhesives, sealants, synthetic fibers, seals, gaskets, carpet underlay, and hard plastic parts.

Another embodiment of the present invention is directed to a manufactured material or product comprising a polyurethane derived from a mixture of at least two polymerized diisocyanates, wherein the material or product is a wood-based composite panel, an oriented strand board (OSB), a medium-density fiberboard (MDF), a plywood panel, a flexible foam seating material, a rigid foam insulation panel, a microcellular foam seal, a microcellular foam gasket, a durable elastomeric wheel, a durable elastomeric tire, an automotive suspension bushing, an electrical potting compound, an adhesive, a sealant, a fiber, seal a gasket, a carpet underlay, or a hard plastic part. Particular wood-based composites of the present invention include oriented strandboards (OSB), medium density fiberboards (MDF) and plywood panels.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of preparing a mixture of at least two diisocyanates comprising:
    (a) providing a protein source comprising or derived from soy protein, corn, rice bran, or oil seeds;
    (b) processing the protein source to generate a product comprising a biodiesel biofuel and a water/glycerin fraction comprising a mixture of alkyl esters comprising diamino alkyl esters and monofunctionalized alkyl esters;
    (c) separating from the water/glycerin fraction the monofunctionalized alkyl esters to generate a product comprising diamino alkyl esters, and
    (d) reacting the separated mixture of diamino alkyl esters of step (c) with an excess of a phosgene to generate a mixture of diisocyanate derivatives of Formula II

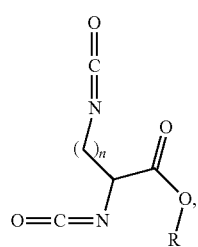

wherein R is an alkyl, and n=1–4
wherein the reaction to generate a mixture of diisocyanate derivatives from the mixture of diamino alkyl esters comprises conditions of temperatures between about 50 to 200° F. and pressures of between 1 to 10 bar.

2. The method of claim 1, wherein at least one of the diisocyanates produced is an alkyl 2,6-diisocyanatohexanoate, an alkyl 2,3-diisocyanatopropanoate, an alkyl 5-(3 formylguanidino)-2-isocyanatopentanoate, or an alkyl 2,4-diisocyanatobutanoate.

3. The method of claim 1, wherein at least one of the diisocyanates produced is a methyl 2,6-diisocyanatohexanoate, a methyl 2,3-diisocyanatopropanoate, a methyl 5-(3-formylguanidino)-2-isocyanalopentanoate, or a methyl 2,4-diisocyanatobutanoate.

4. The method of claim 1, wherein the naturally occurring protein source comprises a soy protein source, a corn, a rice bran, an oil seed, an algae, a grain, a sorghum, or a combination thereof.

5. The method of claim 1, wherein the mixture of diamino alkyl esters is reacted with an excess of a di-phosgene, a tri-phosgene or both, to generate a mixture of diisocyanate derivatives from the mixture of diamino alkyl esters.

6. The method of claim 1, wherein the mixture of diamino alkyl esters comprises a diamino methyl ester.

7. The method of claim 1, wherein the mixture of diamino alkyl esters comprises the diamino alkyl esters of a lysine, an asparagine, an arginine and a glutamine.

8. The method of claim 1, wherein the separating of the 50% monofunctionalized alkyl esters from the water/glycerin fraction comprises use of an ion exchange or a chromatographic separation.

9. The method of claim 1, wherein the separating of the 50% monofunctionalized alkyl esters from the water/glycerin fraction comprises use of a batch or a continuous mode process.

10. The method of claim 1, wherein a product comprising the mixture of diamino alkyl esters is generated by reacting a feedstock source with an alcohol under pressure.

11. The method of claim 10, wherein the process comprises reacting the feedstock source with an alcohol and an acid in a pressure reactor system that allows for sufficient temperature to keep the alcohol from boiling in the presence of an acid catalyst.

12. The method of claim 11, wherein the pressure in the pressure reactor system is 20 PSIG over the vapor pressure of the alcohol.

13. The method of claim 1, further comprising mixing or formulating the mixture of diisocyanate derivatives with a silica, a wax, an antifoamer, a lubricant, a plasticizer, a softening agent, a pigment, a biocide, a filler or a combination thereof.

14. The method of claim 1, further comprising making a manufactured material or a product of manufacture using or incorporating the mixture of diisocyanate derivatives.

15. The method of claim 14, wherein the manufactured material or the product of manufacture is an oriented strand board (OSB).

16. The method of claim 14, wherein the manufactured material or the product of manufacture is a medium density fiberboard (MDF).

17. The method of claim 14, wherein the manufactured material or the product of manufacture is a plywood panel or a wood-based composite panel.

18. The method of claim 14, wherein the manufactured material or the product of manufacture is a flexible foam seating material, a rigid foam insulation panel, a microcellular foam seal, a microcellular foam gasket, or a durable elastomeric wheel.

19. The method of claim 14, wherein the manufactured material or product of manufacture is a durable elastomeric tire or an automotive suspension bushing.

20. The method of claim 14, wherein the manufactured material or product of manufacture is an electrical potting compound, an adhesive, a sealant, a fiber, seal, a gasket, a carpet underlay, or a hard plastic part.

* * * * *